United States Patent
Citernesi et al.

(10) Patent No.: US 10,117,822 B2
(45) Date of Patent: Nov. 6, 2018

(54) CROSS-LINKED HYALURONIC ACID, PROCESS FOR THE PREPARATION THEREOF AND USE THEREOF IN THE AESTHETIC FIELD

(71) Applicant: I.R.A. ISTITUTO RICERCHE APPLICATE S.R.L., Usmate Velate (IT)

(72) Inventors: Ugo Raffaello Citernesi, Airuno (IT); Lorenzo Beretta, Lesmo (IT); Lorenzo Citernesi, Airuno (IT)

(73) Assignee: I.R.A. ISTITUTO RICERCHE APPLICATE S.R.L., Usmate Velate (IT)

( * ) Notice: Subject to any disclaimer, the term of this patent is extended or adjusted under 35 U.S.C. 154(b) by 115 days.

(21) Appl. No.: 14/905,660

(22) PCT Filed: Jul. 16, 2014

(86) PCT No.: PCT/EP2014/065237
§ 371 (c)(1),
(2) Date: Jan. 15, 2016

(87) PCT Pub. No.: WO2015/007773
PCT Pub. Date: Jan. 22, 2015

(65) Prior Publication Data
US 2016/0158140 A1    Jun. 9, 2016

(30) Foreign Application Priority Data
Jul. 16, 2013  (IT) ................. MI2013A1193

(51) Int. Cl.
| | | |
|---|---|---|
| *A61K 8/73* | (2006.01) | |
| *A61L 27/20* | (2006.01) | |
| *A61Q 19/08* | (2006.01) | |
| *C08B 37/08* | (2006.01) | |
| *A61K 8/42* | (2006.01) | |

(52) U.S. Cl.
CPC ............... *A61K 8/735* (2013.01); *A61K 8/42* (2013.01); *A61L 27/20* (2013.01); *A61Q 19/08* (2013.01); *C08B 37/0072* (2013.01); *A61K 2800/74* (2013.01); *A61K 2800/91* (2013.01); *A61K 2800/95* (2013.01); *A61L 2400/06* (2013.01); *A61L 2430/34* (2013.01)

(58) Field of Classification Search
CPC ...... A61K 8/735; A61K 8/42; A61K 2800/91; A61K 2800/74; A61K 2800/95; C08B 37/0072; A61Q 19/08; A61L 27/20; A61L 2400/06; A61L 2430/34
See application file for complete search history.

(56) References Cited

U.S. PATENT DOCUMENTS

| | | | |
|---|---|---|---|
| 5,529,987 A | 6/1996 | Gallina | |
| 5,550,112 A * | 8/1996 | Gallina | ................ A61K 9/0014 514/54 |
| 2005/0136122 A1* | 6/2005 | Sadozai | ................ A61K 31/24 424/493 |

FOREIGN PATENT DOCUMENTS

| | | |
|---|---|---|
| GB | 2151244 A | 7/1985 |
| WO | 2005/067994 A1 | 7/2005 |
| WO | 2012/028863 A1 | 3/2012 |

OTHER PUBLICATIONS

PCT International Search Report and Written Opinion Rule 44.1 corresponding to PCT/EP2014/065237, dated Nov. 12, 2014.
PCT International Preliminary Report on Patentability Rule 71.1 corresponding to PCT/EP2014/065237, dated Jun. 24, 2015.

* cited by examiner

*Primary Examiner* — Layla D Berry
*Assistant Examiner* — Dale R Miller
(74) *Attorney, Agent, or Firm* — LeClairRyan PLLC (57) ABSTRACT

The present invention relates, in one aspect, to the use as dermal filler of a cross-linked biopolymer compatible with the tissues of the human organism based on hyaluronic acid cross-linked with urea. The biopolymer of hyaluronic acid and urea may be applied or injected in a soft tissue of human body for tissue augmentation.

10 Claims, 10 Drawing Sheets

CROSS-LINKED HYALURONIC ACID, PROCESS FOR THE PREPARATION THEREOF AND USE THEREOF IN THE AESTHETIC FIELD

This application is a national stage application under 35 U.S.C. § 371 of PCT Application No. PCT/EP2014/065237, filed Jul. 16, 2014, which claims the priority benefit of Italy Patent Application No. MI2013A001193, filed Jul. 16, 2013, which is hereby incorporated by reference in its entirety.

FIELD OF THE INVENTION

The present invention relates to the use of a cross-linked hyaluronic acid in the aesthetic field and to the process of preparation thereof.

In particular the present invention originates in the field of dermatological fillers, and of biologically compatible polymeric materials useful in the aesthetic non-surgical procedures on the human body.

STATE OF THE ART

Hyaluronic acid is a non-sulphate glycosaminoglycan, that is a linear polysaccharide consisting of monomer units of D-glucuronic acid and D-N-acetylglucosamine.

In the beginning, hyaluronic acid was extracted and then purified from roosters comb or umbilical cord of certain mammalians. With these techniques, a polymer having a variable molecular weight between 1 and 6 million Dalton was obtained.

Currently, hyaluronic acid is obtained microbiologically by means of bacterial fermentation with suitably selected bacterial strains. The average molecular weight of the polymer obtained by the microbiological techniques may range from thousands to millions of Dalton. The viscosity of an aqueous solution of hyaluronic acid increases upon increase of the molecular weight and concentration by determining an increase of the elastic features.

Hyaluronic acid, in particular in the form salified with sodium is water-soluble and is naturally present at the level of the extracellular matrix and in different tissues of the human organism, such as epithelial, connective, nerve tissue, and is further present in synovial and inter-articular fluids.

At the level of the epithelium, hyaluronic acid has numerous functions, for example, it contributes to its hydration, to the organisation of the extracellular matrix, participates in the repair mechanisms of epidermal tissue and the dermal and connective ones as well and further has the function of a filler material.

However, the level of hyaluronic acid present in the various layers of skin decreases over time because of the natural ageing process of the organism. This process may also be affected by external factors, such as exposure to ultra-violet rays of the sun, and to polluting substances and in general to substances having an oxidant activity.

The reduction in the amount of hyaluronic acid and the salts thereof in the skin accelerate skin ageing. Although skin ageing is determined by multiple factors, among which lifestyle, diet, consumption of alcohol and tobacco, the influence exerted by atmospheric agents on the skin has a significant importance. Skin ageing typically shows with atrophy, dryness and loss of elasticity of the skin and the onset of wrinkling and roughness.

In several cases skin ageing determines the formation of small structural failures, the creation of depressions or softening of the tissues especially at the level of the skin and face.

One of the techniques aimed at obviating these aesthetic drawbacks provides the use of dermal fillers, polymer-based products. Their use in the cosmetic-dermatological field is aimed at replacing or integrating the loss of polymers naturally present in the endogenous matrix or at rebalancing the function of those polymers of the skin tissue matrix that are still intact.

Among the filler materials widely used in the aesthetic field, there has been known for a long time the use of collagen and, in recent times, of hyaluronic acid.

Generally, these polymer-based fillers are applied by means of a subcutaneous implant or injection.

For these types of application, the dermal polymer fillers are generally formulated in a form suitable to be injected subcutaneously in the areas wherein it is necessary to obtain a filling or structuring effect.

Initially, hyaluronic acid used as dermal filler consisted of the naturally occurring polymer which typically has a non-cross-linked form.

However, the naturally occurring hyaluronic acid, despite having the advantage of being highly compatible with the tissues of the human body, having a high affinity with water and performing a strong moisturising function, it does not have adequate bio-mechanical properties. For this reason, it does not perform an adequate structuring function and exerts only minimally the effect required for the main applications in the aesthetic field.

It was, in fact, found that the high solubility of hyaluronic acid determines a rapid clearance of the same. When hyaluronic acid is injected into skin tissues, there is a rapid in vivo degradation by both hyaluronidases (enzymatic degradation) and free radicals (chemical degradation) present in the tissues of the human body.

This degradation process forces to use frequent applications of hyaluronic acid to keep the moisturising and structuring effect constant.

In order to overcome these drawbacks, new cross-linked hyaluronic acid-based dermatological fillers have been made, provided with greater consistency as compared to naturally occurring hyaluronic acid. These cross-linked polymers tend to remain longer in the area of implantation and consequently determine an improvement in the filling qualities of skin tissues.

Cross-linked hyaluronic acid-based polymers are obtained with methods that allow forming covalent or ionic bonds that create a tidy network of hyaluronic acid chains.

Depending on the purposes it is then possible to produce cross-linked hyaluronic acid with different degrees of cross-linking. For instance for medical applications, such as in ophthalmic surgery, cross-linked linear polymers are used, while for the formation of structural implants branched hyaluronic acid is used.

Typical examples of cross-linking agents currently used to generate cross-linked hyaluronic acid are divinyl sulfone (DVS), 1,4-butanediol diglycidyl ether, water-soluble carbodiimides and cross-linking agents containing multiple amine groups.

It was however found that these cross-linking agents do not have an adequate biocompatibility with the tissues of the organism, thus when implanted in the skin they may determine the occurrence of adverse reactions or a certain cellular toxicity.

Consequently, there is still a need of providing new cross-linked polymers usable as dermatological fillers that have a high biocompatibility with skin tissues.

One of the purposes of the present invention, therefore, is to provide a cross-linked polymer implantable or injectable in the areas of the skin affected by the signs of skin ageing that is both compatible with skin tissue and possesses adequate filling properties. Another object of the invention is to provide a biocompatible injectable cross-linked polymer that has applications as a restructuring and filling material in the aesthetic field.

SUMMARY

Within the scope of the present invention, there is thus provided a cross-linked biopolymer highly compatible with the skin tissue, methods for the preparation thereof and uses in the aesthetic field of the cosmetic or medical type.

The present invention origins from having found a way for obtaining hyaluronic acid in the cross-linked form using a selected biocompatible cross-linking agent and from having found that a polymer cross-linked with urea is highly biocompatible and resistant to enzymatic or chemical degradation.

In view of the above aims, the present invention relates, in a first aspect, to a cross-linked biopolymer compatible with the tissues of the human organism based on hyaluronic acid cross-linked with urea.

Typically, the cross-linked biopolymer of the invention is injectable or implantable in the tissues of the human organism, such as for example skin.

Typically, the cross-linked biopolymer of the invention is a cross-linked macromolecular matrix highly biocompatible and/or physiologically acceptable.

In accordance with a second aspect, the present invention provides a method of producing a cross-linked biopolymer comprising the cross-linking of hyaluronic acid and urea. Typically, the cross-linking reaction of the method of the invention takes place in acid catalysis.

In certain embodiments, hyaluronic acid and urea are cross-linked in reaction conditions wherein both substances are initially soluble in an aqueous solution.

In accordance with a third aspect the present invention provides a cross-linked biopolymer compatible with the tissues of the human organism based on hyaluronic acid cross-linked with urea for use in the aesthetic field, such as, for example, in the applications in the field of aesthetic medicine.

In certain embodiments, the cross-linked biopolymer based on hyaluronic acid cross-linked with urea is for external use, for example, by means of application to the skin, in a cosmetically effective amount.

In some embodiments, the biocompatible cross-linked biopolymer based on hyaluronic acid cross-linked with urea is injected or implanted in a tissue of the human organism in an amount suitable for determining an aesthetic effect.

In one aspect the present invention provides a method for tissue augmentation in a subject comprising the injection or implantation in a tissue of the subject of a cross-linked biopolymer based on or consisting essentially of hyaluronic acid cross-linked with urea.

In certain embodiments the tissue is a soft tissue of the human body.

In certain embodiments the method for tissue augmentation is for the treatment of lines, wrinkles, folds or furrows associated with face aging of a subject.

BRIEF DESCRIPTION OF THE DRAWINGS

The present invention will be described in detail below and with reference to the figures, wherein.

DETAILED DESCRIPTION OF THE INVENTION

The applicant founds that a biopolymer based on cross-linked hyaluronic acid is obtained by using as a cross-linking agent a substance physiologically available in the human body which is highly compatible with the tissues of the human organism.

In accordance with an aspect of the invention a biocompatible cross-linked biopolymer is provided for use for tissue augmentation or as dermal filler for improvement of the aesthetic appearance of an anatomical feature of an individual wherein said biopolymer is based on hyaluronic acid cross-linked with urea.

In accordance to a further aspect the present invention provides a soft tissue filler augmentation biopolymer comprising hyaluronic acid cross-linked with urea and the use thereof as dermal filler for treating aging, especially aging face.

In some embodiments, the cross-linked biopolymer based on hyaluronic acid cross-linked with urea has a molecular weight comprised in the range from 100,000 to 20,000,000 Dalton, 500,000 to 10,000,000 Dalton, 1,000,000 to 6,000,000 Dalton, typically from 2,000,000 to 4,000,000 Dalton.

Typically, the hyaluronic acid from which the cross-linked biopolymer of the invention derives is a polysaccharide consisting essentially of alternating units of glucuronic acid and N-acetyl glucosamine capable of retaining water and withstanding hydrostatic stresses.

In certain embodiments the starting hyaluronic acid is non-immunogenic and has the advantage of being physiologically acceptable and compatible with the tissues of the human body.

The cross-linking agent used to obtain the cross-linked biopolymer of the invention is based on urea (carbamide), an organic compound having two amino functionalities ($-NH_2$) joined together with a carbonyl functional group ($C=O$). Urea plays a key role in the nitrogen metabolism of many mammalians, being the main nitrogenous compound found in the urine of such mammalians and appears like an odourless and colourless water-soluble, substantially non-toxic substance. Urea further has a high solubility in an aqueous environment, due to the capability of forming hydrogen bonds with water.

The cross-linked biopolymer of the invention may be prepared by cross-linking hyaluronic acid or a salt thereof with urea, preferably in an acidic environment.

In accordance with a second aspect of the invention, there is thus provided a method of producing a biopolymer based on hyaluronic acid cross-linked with urea comprising a polymerization step of hyaluronic acid or a salt thereof with urea under acidic conditions.

In certain environmental conditions, hyaluronic acid and urea may be combined in a water-based liquid wherein both the components are soluble. Hyaluronic acid and the salts thereof and urea may then be cross-linked while they are both dissolved in a water-based liquid to form the biopolymer of the invention.

Suitable liquids used in the method of the invention comprise water and saline.

In general, the method of the invention provides a dissolution step wherein hyaluronic acid or a salt thereof is dissolved in a liquid, typically water.

In some embodiments, at the end of the dissolution step, the hyaluronic acid in solution is present in an amount ranging from 2 mg/ml to 120 mg/ml, 5 to 25 mg/ml, typically from 7 to 20 mg/ml.

Within the scope of the invention the term salt of hyaluronic acid means any water-soluble salt of hyaluronic acid such as for example sodium, potassium or calcium salt.

Within the scope of the invention the term biopolymer means a physiologically acceptable polymer, i.e. compatible with the tissues of the human organism.

In certain embodiments, the starting hyaluronic acid or a salt thereof has a molecular weight as previously described for the biopolymer based on hyaluronic acid cross-linked with urea, obtained at the end of the cross-linking process.

The method of the invention further comprises a dissolution step of urea in an aqueous solution, preferably at acidic pH for example of from 3 to 6.8 typically of 3.5 to 4.

In accordance with some embodiments, the urea in acidic aqueous solution is present at a concentration from 1 to 100 mg/ml, 3 to 50 mg/ml, typically from 5 to 25 mg/ml.

In a subsequent step of the method, the solution based on hyaluronic acid and the solution which typically is an acidic solution based on urea are placed in contact to form a mixture to give the biopolymer crosslinked with an amidic type bond. In accordance with certain embodiments, the mixture obtained is stirred to obtain a biopolymer based on hyaluronic acid cross-linked with urea.

Typically the reaction conditions of the method of the invention, such as, for example, the concentration of the two components, the pH of the solution, may be adjusted to prevent the formation of complexes that precipitate from the solution and prevent or slow down the cross-linking.

For example, the weight ratio of hyaluronic acid or a salt thereof to urea in the aqueous solution or in the cross-linking reaction mixture may be in the range from 0.3 to 10, 0.8 to 5, 1 to 3.

In some embodiments, the mixture obtained has a pH in the range from 3 to 6.8 preferably from 3.5 to 4. In some embodiments to obtain the acidic pH of the solution, an acidic solution is added, such as for example a HCl aqueous solution.

Optionally, if the mixture has a pH outside of the range 3.5-4 it is possible to add a pH adjusting agent, such as a solution of an acid, for example HCl, or a base, for example NaOH.

In some embodiments in order to adjust the pH in the range 3.5-4 it is possible to add a buffer, such as, for example, acetic acid and sodium acetate. The Applicant also founds that carrying out the reaction at a pH acidic in the range of 3.5 to 4 an unexpected high rate cross linking of hyaluronic acid is achieved.

In some embodiments, the mixture is thermostated, for example, at 35(+/−2)° C. for 20-24 hours and subsequently subjected to swelling to eliminate the excess of urea present in the solution.

In accordance with some embodiments, the pH of the product obtained is in the range from 5.5 to 7.5, typically 5.5 to 6.8. If the pH does not fall within the range 5.5-7.5 it is possible to adjust it adding a solution of 0.2M NaOH, in one or more portions, until it falls within the desired range.

In certain embodiments, at the end of the cross-linking reaction the biocompatible cross-linked biopolymer obtained is reduced to particles or homogenized by passing through a screen having a suitable pore size, for example from 5 to 150 microns, or 40 to 80 microns to form a hydrogel or an injectable suspension.

In accordance with some embodiments the biopolymer newly formed from the polymerization reaction is in the form of a hydrogel.

In some embodiments, the biocompatible cross-linked biopolymer based on hyaluronic acid cross-linked with urea obtained with the method of the invention is sterilized or freeze-dried.

The biocompatible cross-linked biopolymer based on hyaluronic acid cross-linked with urea has application both in the cosmetic field, for example as a wrinkle or skin roughness filler, and in the aesthetic medical field, for example as a dermatological filler or to manufacture subcutaneous implants. The cross-linked biopolymer of the invention is also suitable for the reconstitution of tissues of the human organism that have been removed after surgery, such as, for example, in the case of surgical removal of breast tissue or liposuction.

In accordance with one aspect of the invention, there is provided a cosmetic or aesthetic or medical treatment method for the improvement of the aesthetic appearance of an anatomical feature of an area of the body of an individual, said method comprising the application, injection or implantation on a tissue of a biopolymer made of hyaluronic acid cross-linked with urea. In certain embodiments the method is a non-surgical method of treatment.

The improvement of the aesthetic appearance of an anatomical feature of an individual includes the improvement of any type of aesthetic quality including external appearance, tactile feel, in particular of the skin of any region of the body, such as for example face, lips, periocular area, breasts, buttocks.

In certain aspects a biopolymer consisting essentially of hyaluronic acid cross-linked with urea for use in the treatment of face aging is provided especially for the treatment of lines, wrinkles, folds or furrows associated with face aging wherein the biopolymer is applied or injected in a soft tissue of a human body. In certain embodiments the biopolymer of the invention is applied on the skin or preferably injected or implanted in the epidermis, dermis or hypodermis.

The method of the invention comprises implanting or injecting a cosmetically effective amount of the biocompatible cross-linked biopolymer described hereinabove in a tissue of the human body to improve the aesthetic quality of an anatomical feature.

In certain embodiments the tissue of the human body is a soft tissue.

In some embodiments, the biopolymer injected or implanted in the tissue of the human body is in the form of a hydrogel or suspension.

The present invention shall now be described with reference to the following examples which are provided for illustration purposes and shall not be intended as limiting of the scope of the present invention.

Example 1

Method of Preparation of Hyaluronic Acid Cross-Linked with Urea of the Invention 8 g sodium hyaluronate is dissolved in 72 g saline. A solution is prepared separately dissolving 4 g urea in 0.2M 16 g HCl.

The two solutions prepared are mixed until the final solution is homogeneous; the pH is measured which has to be in the range from 3.5 to 4.

The product is thermostated at 35(+/−2)° C. for 20-24 hours, the excess of urea is then eliminated; once purified, the pH of the product obtained was measured which was comprised from 5.5 to 7.5.

If the pH does not fall within the range 5.5-7.5, it is adjusted adding a solution of 0.2M NaOH until it falls within the desired range.

Example 2

Comparative Example of Preparation of Hyaluronic Acid Cross-Linked with Urea

The same cross-linking procedure of Example 1 was carried out in basic catalysis using a solution of 0.2M NaOH.

8 g sodium hyaluronate is dissolved in 72 g saline. A solution is prepared separately dissolving 4 g urea in 0.2M 16 g NaOH. The two solutions prepared are mixed until the final solution is homogeneous. The product thermostated at 35(+/−2)° C. for 20-24 hours does not cross-link, but instead is hydrolysed leading to a breakage in the molecules of hyaluronic acid whereby the product loses its viscoelastic properties.

Example 3

Chemical-Physical Properties of the Hyaluronic Acid Cross-Linked with Urea Obtained by the Method of Example 1

Features
The product obtained was subjected to the following tests.
Rheological analysis of the product
Determination of viscosity $\eta$
Determination of the Storage Modulus G' and the Loss Modulus G"
Sterilization Strength Test
Freeze drying Strength Test The rheological analyses carried out were performed according to the following modes:
1. Analysis of viscosity $\eta$ and Shear Stress $\tau$ as a function of Shear Rate $\dot{\gamma}$ with the following parameters forward curve of 400 s consisting of 50 points×8 s with Shear Rate $\dot{\gamma}$ from 1 to 50 1/s; constant stretch of 120 s consisting of 12 points×10 s with Shear Rate $\dot{\gamma}$ constant at 50 1/s; backward curve of 400 s consisting of 50 points×8 s with Shear Rate $\dot{\gamma}$ from 50 to 1 1/s
2. Amplitude Sweep analysis with the following parameters 21 points with a sampling frequency established by the instrument, Angular Frequency $\omega$ constant at 10 rad/s with Strain $\gamma$ variable from 0.001 to 100%
3. Frequency Sweep analysis with the following parameters 16 points with a sampling frequency established by the instrument, Strain $\gamma$ constant at 0.7% with Angular Frequency $\omega$ variable from 0.1 to 100 rad/s.

Figure 1:
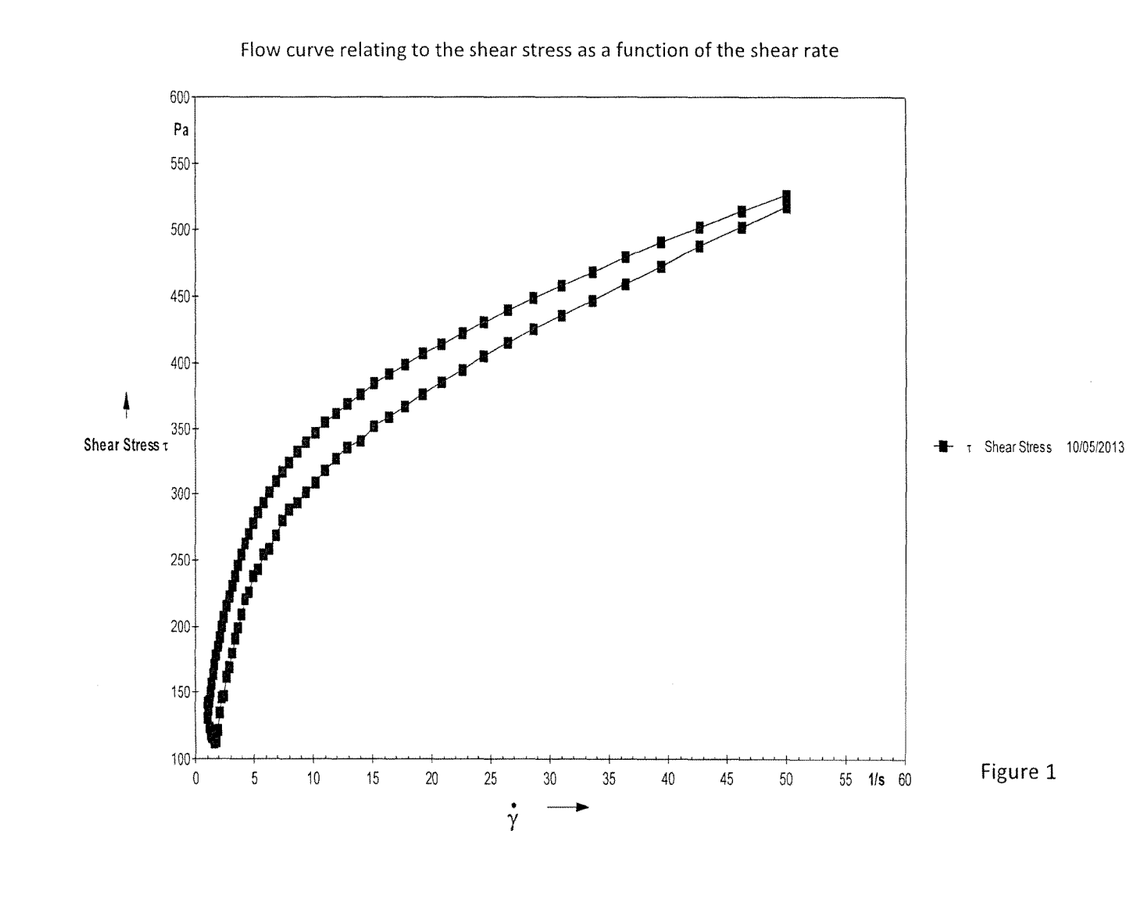
FIG. 1 illustrates flow curves relating to the shear stress—Shear stress τ—as a function of the shear rate γ˙ of the cross-linked biopolymer hyaluronic acid-urea (Ex. 1 and 3)

The first assays were conducted on the non-sterilized product from which there emerges a viscoelastic behaviour with the presence of an area of hysteresis. The analysis of viscosity (FIG. 1), instead, shows how the product obtained is homogeneous, and the degree of cross-linking is even inside the product without the presence of clots or aggregates, both macroscopic and microscopic.

Figure 2:
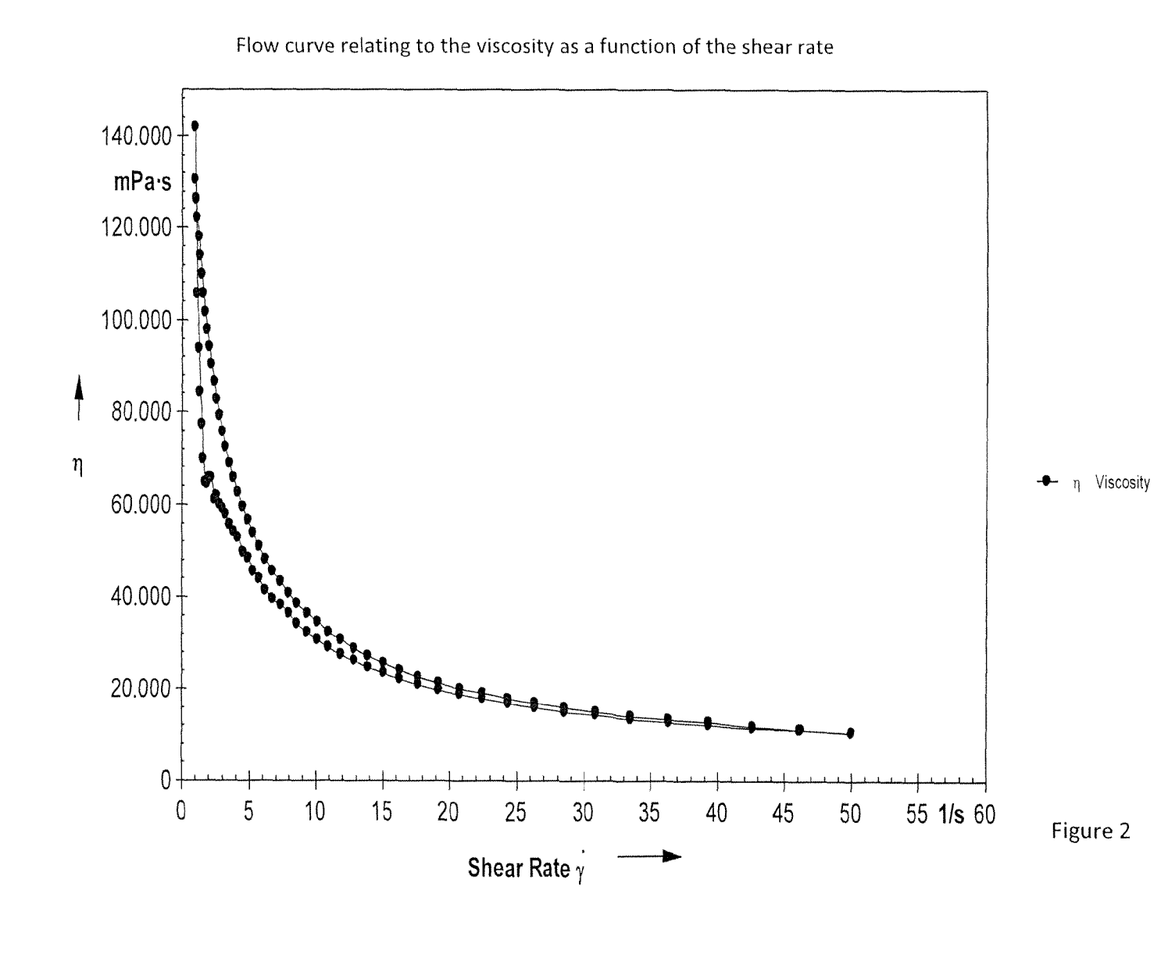
FIG. 2 shows flow curves (Amplitude Sweep assay) relating to the viscosity expressed as mPa as a function of the Shear Rate according to Example 3.
Figure 3:
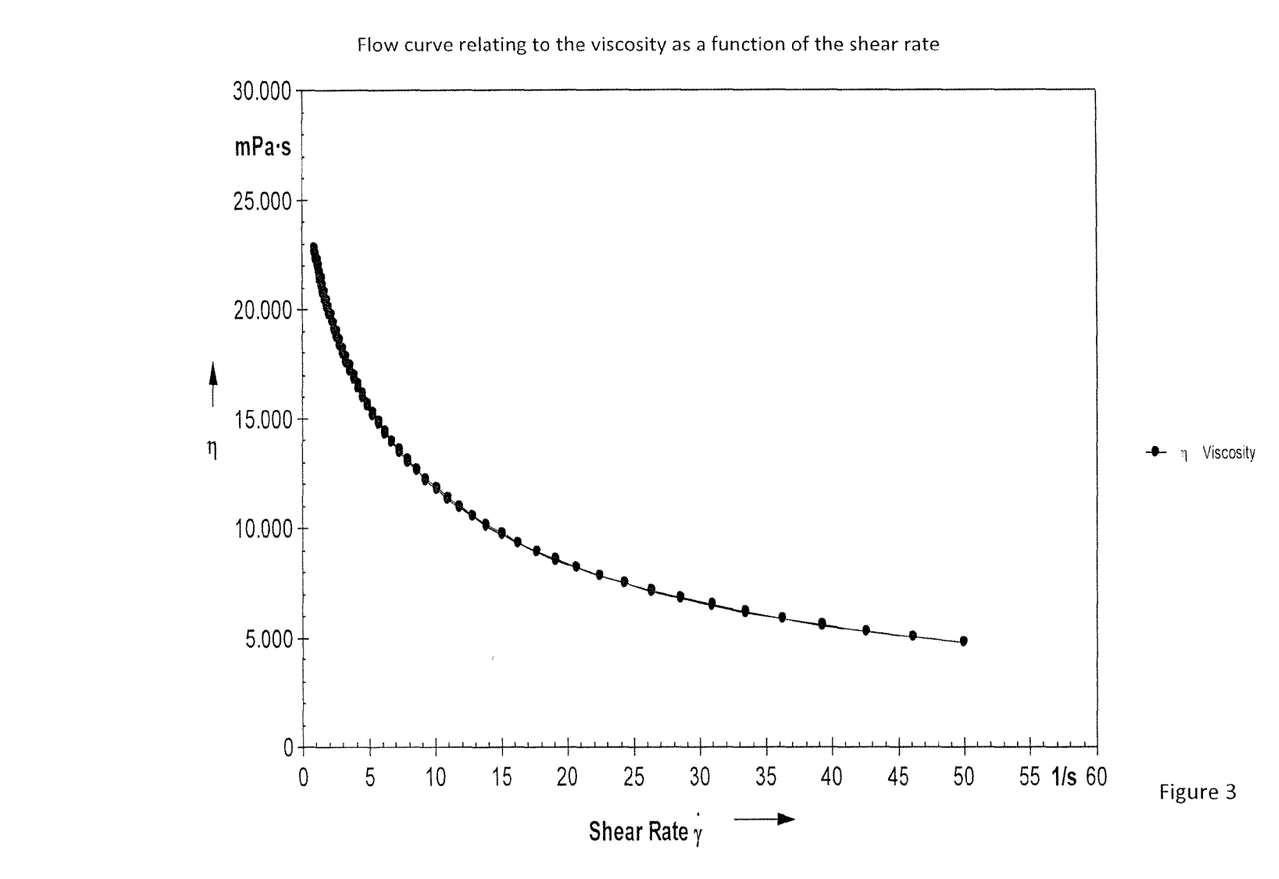
FIG. 3 shows the flow curve relating to the viscosity η as a function of the Shear rate γ˙ of the sterilized biopolymer of Example 4.

On the same sample the analysis in Amplitude Sweep was performed which, as shown in FIG. 2, shows how that elastic feature is prevalent, a datum highlighted by higher values of G' and the absence of a cross-over point between the curve of G' and G".

Example 4

Figure 4:
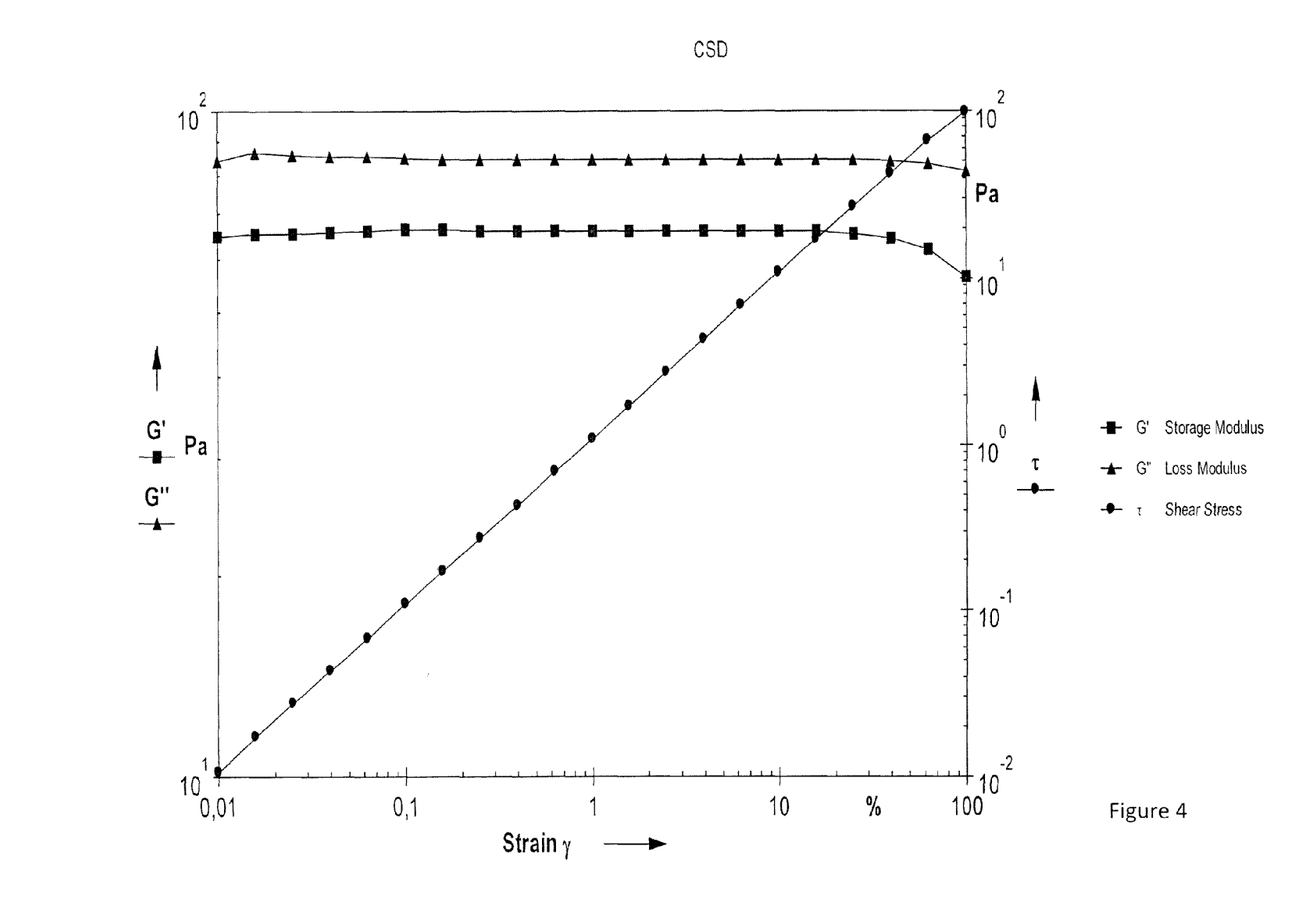
FIG. 4 shows the pattern of the elastic modulus (Storage) of the viscous modulus (loss) of the polymer as a function of determined Strain values: the assay denotes how the elastic modulus (and consequently the elastic behaviour) prevails over the merely viscous one.

The product of Example 1 was subjected to terminal sterilization by means of autoclave for 20 minutes at 121° C., after the treatment, it appears less viscous than the starting product, but retains some rheological features that show once again how the elastic feature is prevalent as compared to the dissipative one. Also in the graphs illustrated in the appended FIGS. 4, 4, relating to the product subjected to sterilization, the presence of an area of hysteresis and the higher value of the G' modulus than G" are shown.

Figure 5:
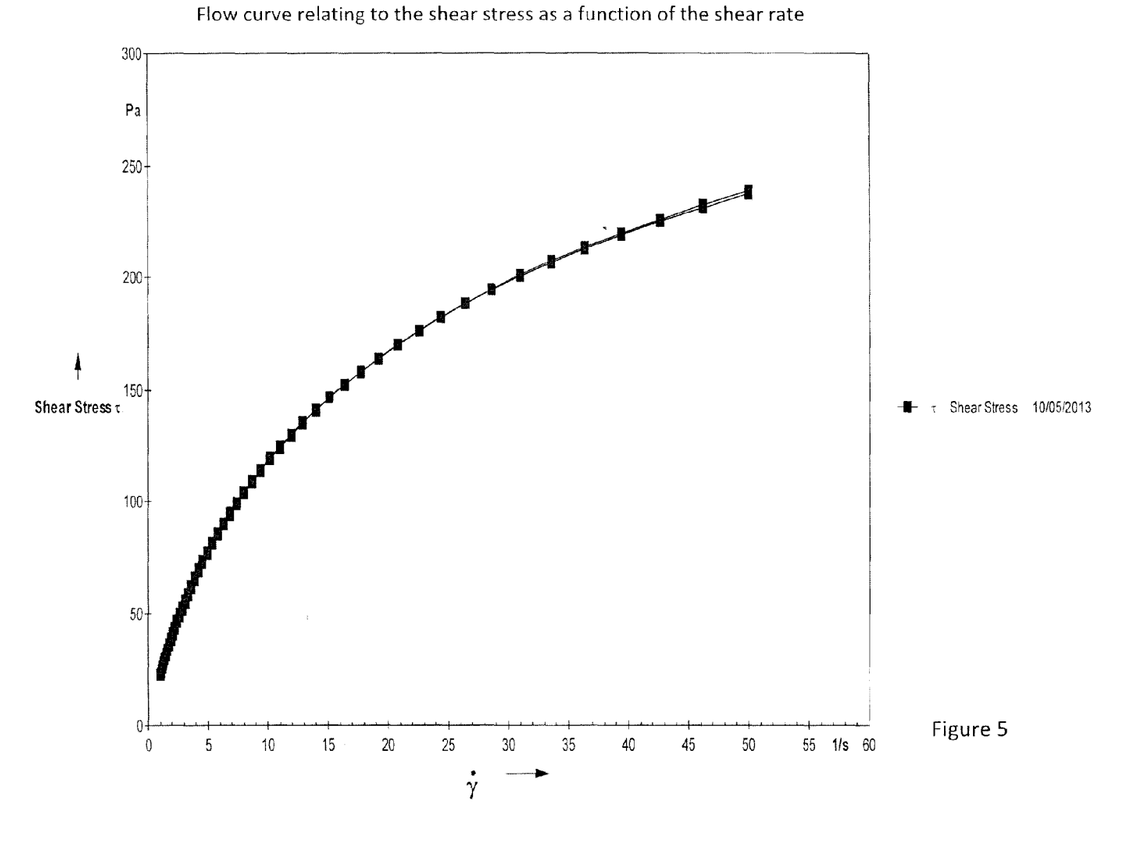
FIG. 5 shows the flow curve relating to the shear stress—Shear stress τ—as a function of the Shear Rate γ˙ according to Example 4.

The graph of the flow curve relating to the Shear Rate $\dot{\gamma}$, illustrated in FIG. 5, instead shows the perfect homogeneity of the product and how the product is capable of returning to the initial status even when subjected to high Shear Rates $\dot{\gamma}$.

Figure 6:
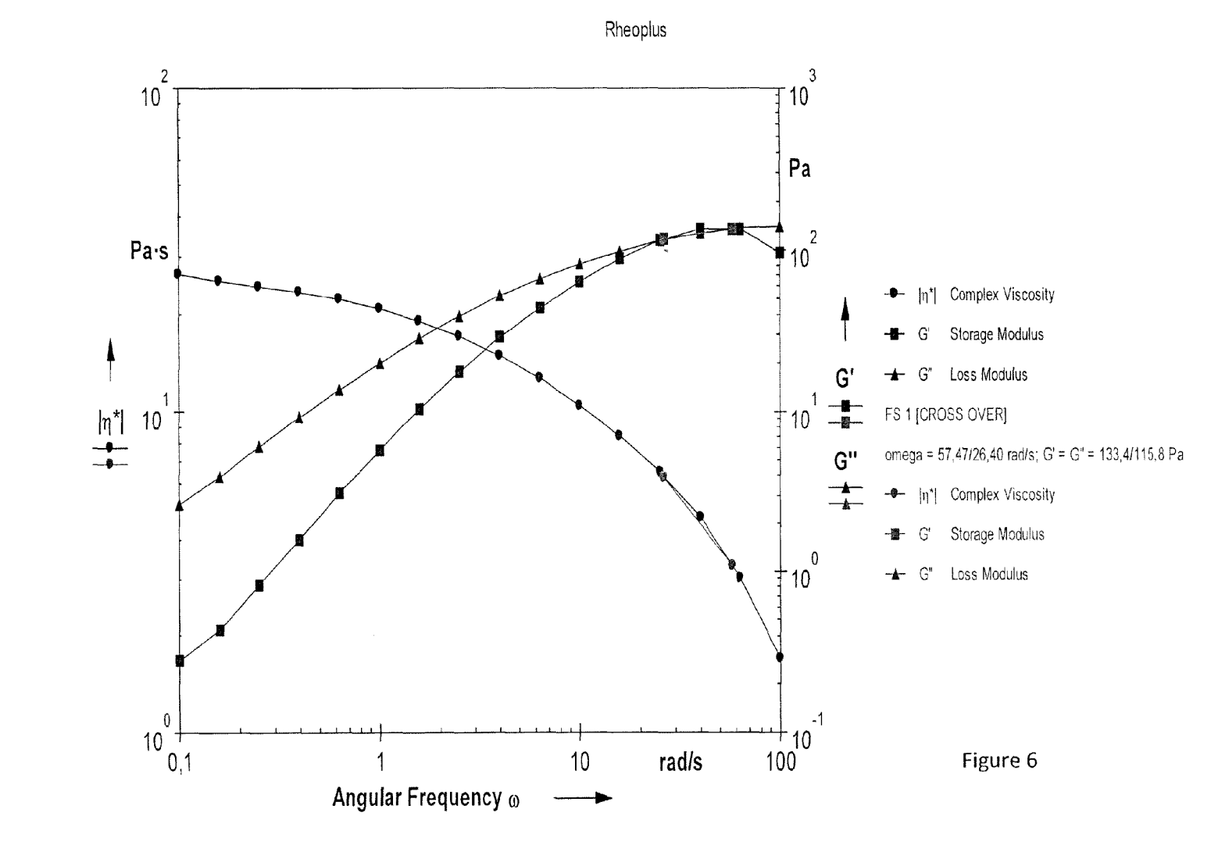
FIG. 6 illustrates the graph in Frequency Sweep of the product considered in Example 4.

The assay in Frequency Sweep illustrated in FIG. 6 on the other hand shows how the product decreases its overall viscosity $|\eta^*|$ upon increase of the angular frequency $\omega$ as is expected by a viscoelastic product; it should also be noted how the G'-G" cross-over only takes place at very high values of angular frequency $\omega$, once again demonstrating that the sterile product does not lose its elastic properties.

Example 5

The product of Example 1 is also resistant to freeze drying, in fact, the procedure of eliminating water and the subsequent rehydration allow obtaining a product with features similar to the one not subjected to freeze drying.

Figure 7:
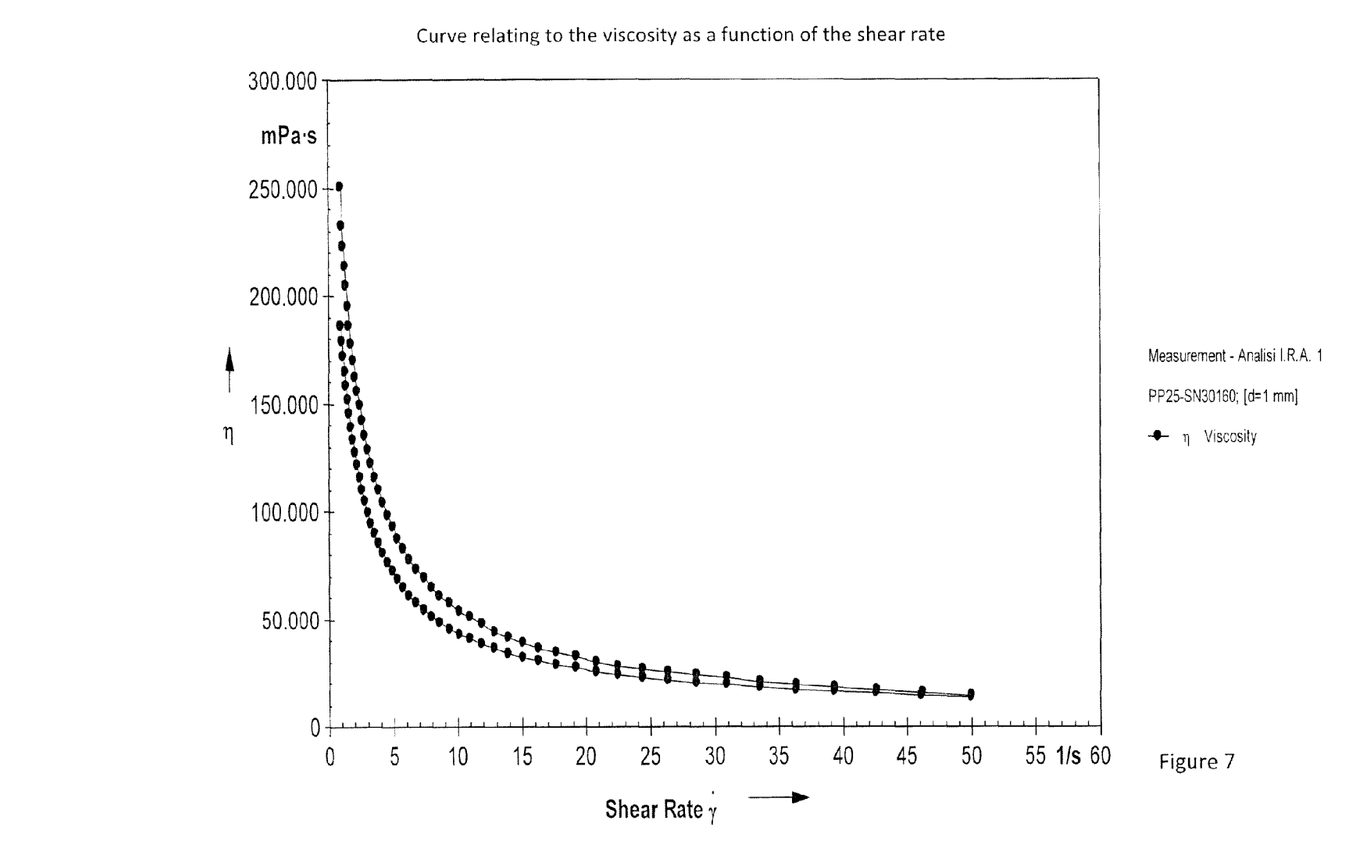
FIG. 7 illustrates curves relating to the viscosity η as a function of the Shear rate γ˙ of the freeze-dried biopolymer of Example 5.
Figure 8:
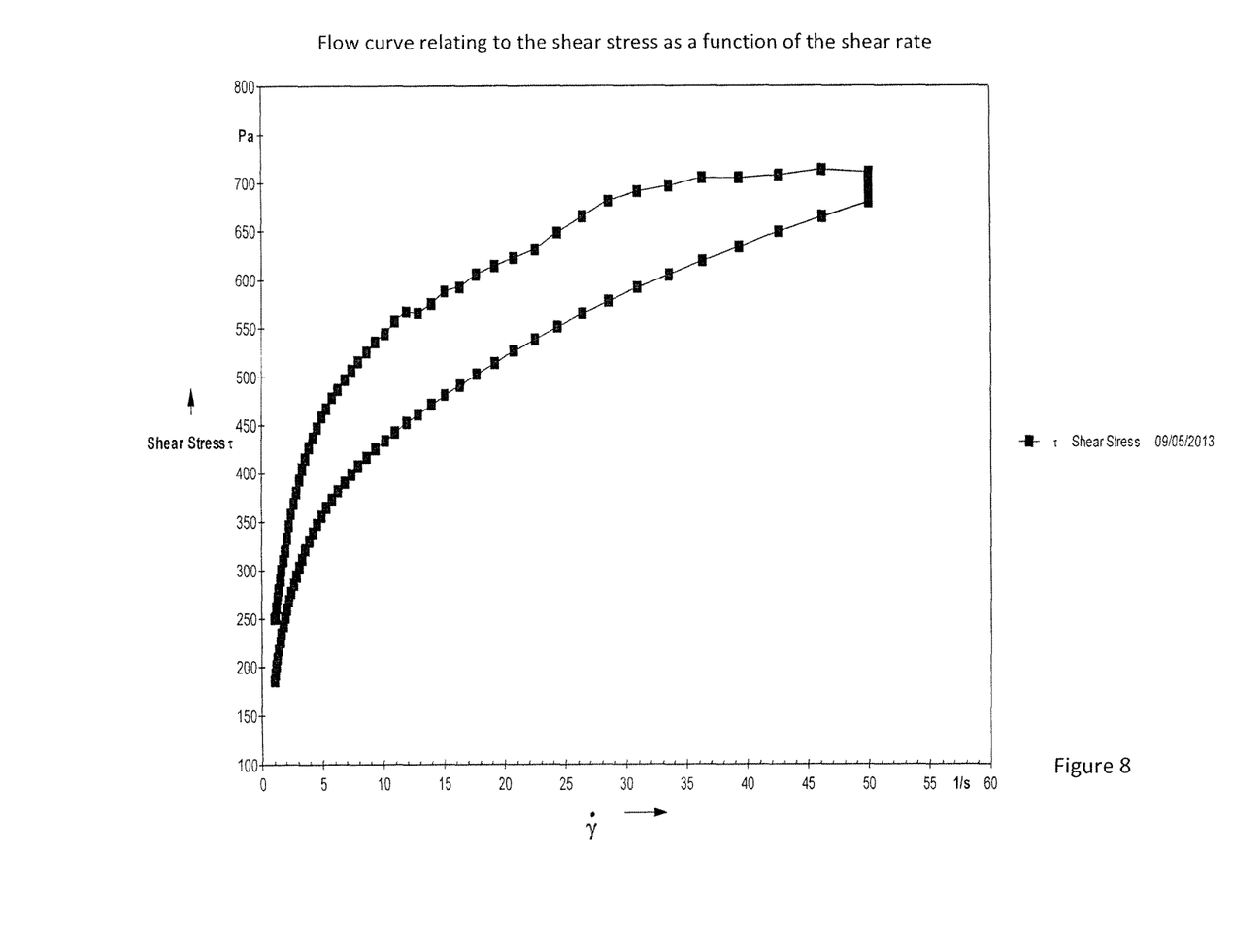
FIG. 8 shows the flow curve relating to the shear stress—Shear stress τ—as a function of the Shear Rate γ˙ of the freeze-dried biopolymer of Example 5.

The assay illustrated in FIGS. 7 and 8 shows how the freeze-dried product still has very high values of viscosity, demonstrating the capability of the product of not degrading with freeze-drying. As regards the shear stress, it is, on the other hand, possible to see how the product remains in its entirety homogeneous, but there are areas wherein the degree of cross-linking is slightly degraded.

Figure 9:
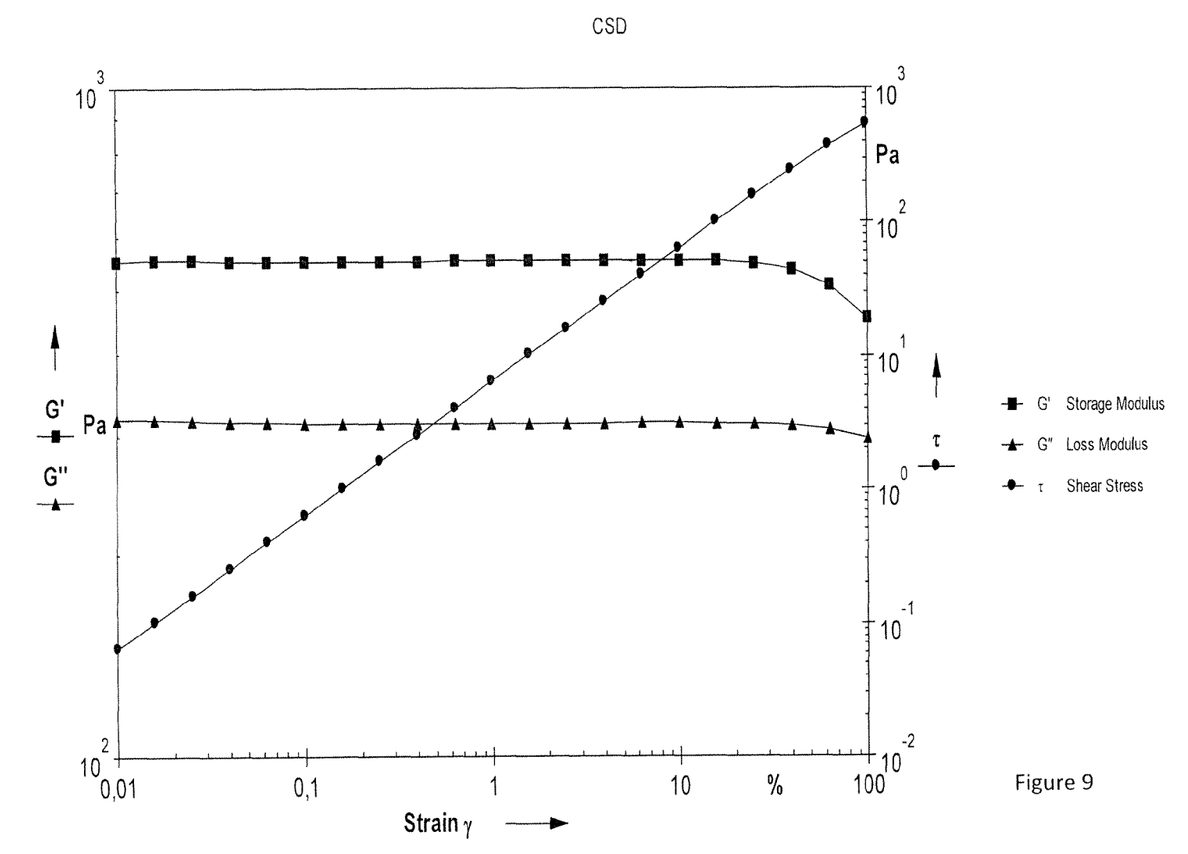
FIG. 9 illustrates a graph in Amplitude Sweep of the freeze-dried product of Example 5.
Figure 10:
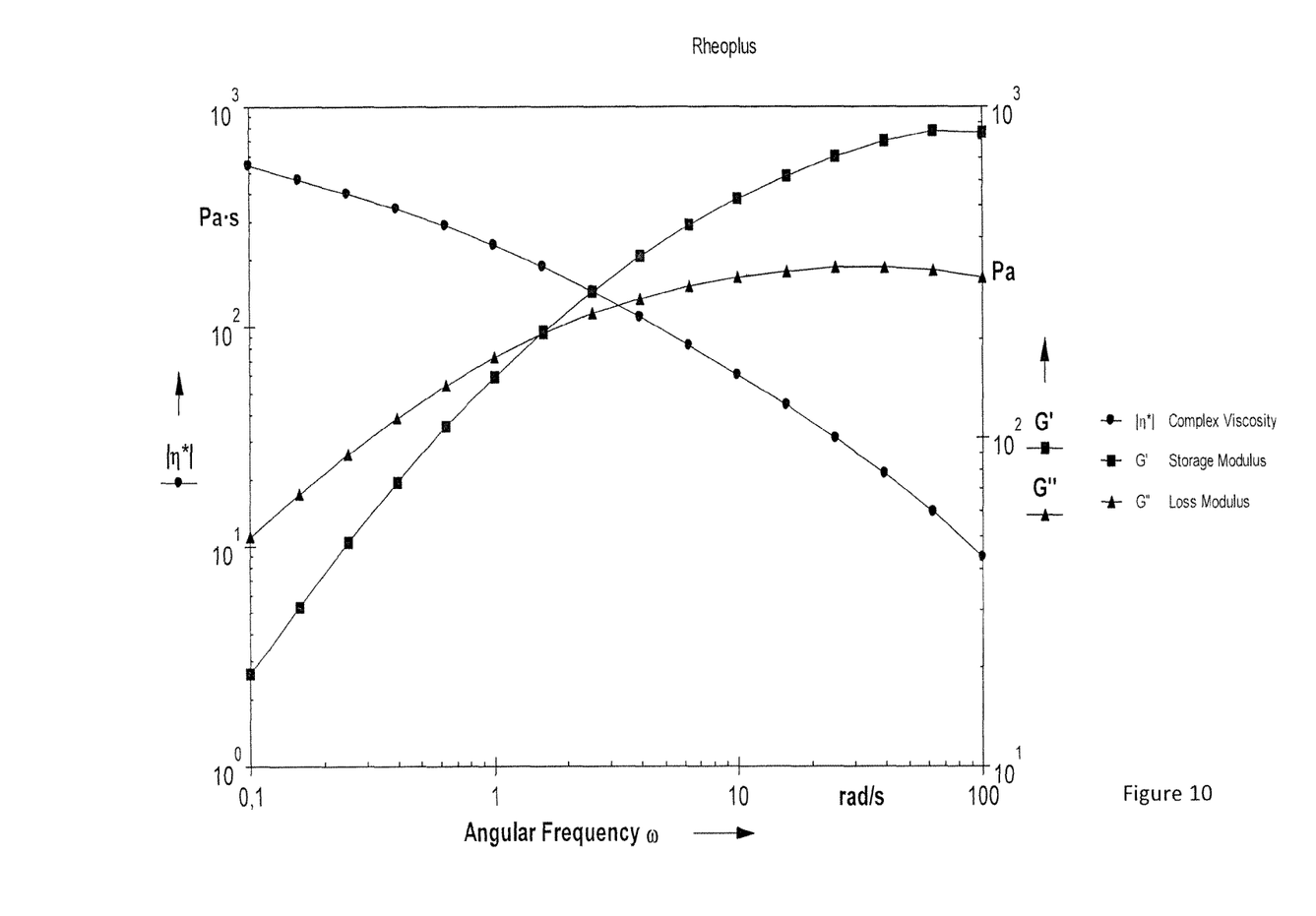
FIG. 10 illustrates a graph in Frequency Sweep of the freeze-dried product of Example 5.

The graphs in Amplitude Sweep and Frequency Sweep reported in FIGS. 9 and 10, relative to the freeze-dried product of Example 1 show how the product does not undergo substantial deterioration in its overall structure but, as mentioned hereinabove, there is a slight degradation of the degree of cross-linking.

The product further appears easily spreadable and shapeable in different shapes depending on the target use. The form in which it is shaped is maintained in the freeze-drying process which, as previously described, is non-destructive and capable of retaining the primary features of the same products.

The invention claimed is:

1. A method for tissue augmentation of an individual, said method comprising:
   injecting under the skin of said individual, a biocompatible cross-linked biopolymer wherein said biopolymer consists of hyaluronic acid cross-linked with urea.

2. A method according to claim 1, wherein the biopolymer has a molecular weight in the range from 100,000 to 20,000,000 Dalton.

3. A method according to claim 1, wherein the biopolymer is in the form of a hydrogel or particles.

4. A method according to claim 1, wherein the biopolymer is injected or implanted in the epidermis, dermis, or hypodermis of said individual.

5. A method according to claim 1, wherein the biopolymer is in the form of an implant or of a subcutaneous filling injection for the treatment of aging.

6. The method of claim 1 for the cosmetic or aesthetic treatment of lines, wrinkles, folds or furrows associated with face aging of a subject in need of an aesthetic treatment.

7. The method of claim 1, wherein the tissue augmentation is for the treatment of lines, wrinkles, folds, or furrows.

8. A method for the manufacture of a hyaluronic acid biopolymer cross-linked with urea said method comprising:
   a) dissolving hyaluronic acid or a salt thereof in a liquid to form a solution of hyaluronic acid;
   b) dissolving urea in an aqueous acidic solution with a pH of 3.5 to 4 to form an acidic aqueous solution of urea;
   c) combining the solution of hyaluronic acid with the acidic aqueous solution of urea to obtain a mixture, said mixture having a pH in the range of 3.5 to 4, wherein said hyaluronic acid biopolymer crosslinked with urea is formed as a result of said combining.

9. The method according to claim 8, wherein the acidic aqueous solution of urea contains HCl preferably in a concentration in the range from 20 to 30% by weight.

10. The method according to claim 8, wherein the hyaluronic acid dissolved in solution is in the form of sodium or calcium salt.

* * * * *